US 6,562,801 B1

(12) United States Patent
Rombel (10) Patent No.: US 6,562,801 B1
(45) Date of Patent: May 13, 2003

(54) PPGPP AND PPPGPP AS IMMUNOMODULATORY AGENTS

(75) Inventor: Irene Rombel, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/549,099

(22) Filed: Apr. 12, 2000

Related U.S. Application Data
(60) Provisional application No. 60/129,665, filed on Apr. 15, 1999.

(51) Int. Cl.$^7$ .................. A01N 43/04; A61K 39/395
(52) U.S. Cl. ................ 514/45; 424/180.1; 424/182.1; 514/44; 514/48
(58) Field of Search .............................. 514/44, 48, 45; 424/180.1, 182.1

(56) References Cited

U.S. PATENT DOCUMENTS

| 4,141,972 A | * | 2/1979 | Nishino et al. ............. 424/180 |
| 4,643,992 A | * | 2/1987 | Goodman et al. ............ 514/45 |
| 5,221,611 A | | 6/1993 | Stenglein et al. ............ 435/7.1 |

FOREIGN PATENT DOCUMENTS

| EP | 112632 | 7/1984 |
| EP | 341066 | 11/1989 |
| JP | 55158557 | 12/1980 |
| WO | WO 94/07904 | 4/1994 |
| WO | WO 98/18810 | 5/1998 |

OTHER PUBLICATIONS

Hamagishi et al, Journal of Biochemistry, 88, 1785–192, 1980).*
Hamagishi, et al, Agric. Biol. Chem. 45(12), 2927–2929, 1981.*

Ada, "Vaccines," In: Paul, E. W., ed. *Fundamental Immunology*, Third Edition, Raven Press, New York, 37:1309–1352, 1993.

Allison and Byars, "Immunological Adjuvants: desirable properties and side–effects," *Mol. Immunol.*, 28:279–284, 1991.

Bomford "Adjuvants in AIDS Vaccines," *The Theory and Practical Application of Adjuvants*, Stewart–Tull, D.E.S., ed., Wiley, Chichester and New York, 16:353–363, 1995.

Cashel, "Preparation of guanosine tetraphosphate (ppGpp) and guanosine pentaphosphate (pppGpp) from *escherichia coli* ribosomes," *Analytical Biochemistry*, 57:100–107, 1974.

Cashel, "Regulation of bacterial ppGpp and pppGpp," *Ann. Rev. Microbiol.*, 29:301–318, 1975.

Davis et al., "DNA–based immunization induces continuous secretion of hepatitis B surface antigen and high levels of circulating antibody," *Human Molecular Genetics* 2:1847–1851, 1993.

Davis, "CpG DNA is a potent enhancer of specific immunity in mice immunized with recombinant hepatitis B surface antigen," *J. Immunol.*, 160:870–876, 1998.

(List continued on next page.)

*Primary Examiner*—Lynette R. F. Smith
*Assistant Examiner*—Vanessa L. Ford
(74) *Attorney, Agent, or Firm*—Fulbright & Jaworski, LLP (57) ABSTRACT

The present invention relates generally to the fields of immunopreventive therapy and vaccine development. More particularly, it concerns compositions and methods of use of the bacterial nucleotides ppGpp and pppGpp and their analogs as adjuvants that can be used to generate more potent and robust vaccines in a shorter period of time, was well as antibodies produced using the disclosed compositions and methods. The inventor has found novel immunomodulatory activities for this group of nucleotides.

14 Claims, 5 Drawing Sheets

OTHER PUBLICATIONS

Elgert, "Immunoenhancement reinforces the immune system," In: *Immunology: Understanding the Immune System*, Wiley–Liss, New York, 371–372, 1996.

Gallant, "Stringent control in E. coli," *Ann Rev. Genetics*, 13:393–415, 1979.

Goodman and Goodman, "Topology of the loxoribine binding site," *J. Immunol.* 153:4081–4087, 1994.

Goodman, "Immunobiologic properties of the C8–derivatized guanine ribonucleosides," *Biomed. Pharmacother.* 37:344–350, 1983.

Gregory and Kern, "Mitogenic response of t–cell subclasses to agarose–linked and to free ribonucleotides," *Immunology* 42:451–457, 1981.

Heeg et al., "Bacterial dna as an evolutionary conserved ligand signalling danger of infection of immune cells," *Eur. J. Clin. Microbiol. Infec. Dis.*, 17:464–469, 1998.

Krieg et al., "CpG motifs in bacterial dna trigger direct b–cell activation," *Nature*, 374:546–549, 1995.

Lindblad, "Aluminium Adjuvants," *The Theory and Practical Application of Adjuvants*, Stewart–Tull, D.E.S., ed., Wiley, Chichester and New York, 16:353–363, 1995.

Lipford et al., "Bacterial dna as immune cell activator," *Trends Microbiol.*, 6:496–500, 1998.

Livingston, "Approaches to augmenting the immunogenicity of melanoma gangliosides: from whole melanoma cells to ganglioside–klh conjugate vaccines," *Immunol. Rev.*, 145:147–166, 1995.

Marrack and Kappler, "Subversion of the immune system by pathogens," *Cell*, 76:323–332, 1994.

Reitz et al., "Small–molecule immunostimulants. Synthesis and activity of 7,8–disubstituted guanosines and structurally related compounds," *J. Med. Chem.* 37:3561–3578, 1994.

Roitt et al., In: *Immunology*, Mosby, London, 19.8–19.9, 1996.

Roitt, In: *Essential Immunology*, Blackwell Scientific Publications, London. 288–292, 1994.

Scheuer et al., "Enhancement of the in Vivo antibody response by an 8–derivatized guanine nucleoside," *Cell. Immunol.* 91:294–300, 1995.

Singh and O'Hagan, "Advances in vaccine adjuvants," *Nature Biotechnology*, 17:1075–1079, 1999.

Sjolander et al., "ISCOMS: anadjuvant with multiple functions," *J. Leuco. Biol.*, 64:713–723, 1998.

Stewart–Tull, "The use of adjuvants in experimental vaccines," *Vaccine Protocols*, Humana Press, Totowa, New Jersey, 9:135–139, 1996.

Subbarao et al., "Rescue of an influenza a virus wild–type PB2 gene and a mutant derivative bearing a side–specific temperature–sensitive and attenuating mutation," *J. Virol.* 67:7223–7228, 1993.

* cited by examiner

Comparison of humoral response with ppGpp vs. CpG oligonucleotide

PPGPP AND PPPGPP AS IMMUNOMODULATORY AGENTS

This application claims the benefit under 35 U.S.C. §119(e) of provisional application Serial No. 60/129,665, filed Apr. 15, 1999, now abandoned.

BACKGROUND OF THE INVENTION

1. Field of the Invention

The present invention relates generally to the fields of immunopreventive therapy and vaccine development. More particularly, it concerns the development of novel adjuvants that can be used to generate more potent and robust vaccines. The application also describes the kinetic modulation of the immune response by these novel adjuvants.

2. Description of Related Art

Adjuvants for immunization are well known in the art and attempts to develop safe and effective adjuvants is an ongoing challenge. One of the main problems with current adjuvants is that most are unsuitable for use in human vaccines. One of the first adjuvant developed was Freund's complete adjuvant which is a water-in-oil emulsion containing killed mycobacteria. This is unsuitable for use in humans due to severe side effects such as the lifelong persistence of oil in the tissues and the occasional production of sterile abscesses. Freund's complete adjuvant has excellent immunopotentiating properties, but the side effects are so severe that it renders the use of this adjuvant unacceptable in humans (and sometimes in animals).

Other bacterially-derived adjuvants, such as MDP and lipid A are also associated with undesirable side-effects, and efforts are currently underway to develop benign analogs of these compounds (Roitt, 1994; Elgert, 1996). Oil based adjuvants in general are less desirable because they create undesirable side-effects such as visceral adhesions and melanized granuloma formations and because they cannot form a homogeneous mixture with DNA preparations such as DNA-based vaccines.

Aluminum salt-based adjuvants (such as alum) have excellent safety records but have the important disadvantages that they have a mediocre record in terms of efficacy with some antigens (Sjolander et al., 1998).

Oligonucleotides having unmethylated CpG dinucleotides have been shown to activate the immune system (A. Krieg, et al., 1995). CpG motifs may be inserted into a plasmid DNA vaccine vector, and replicated in bacteria thereby allowing the CpG motifs to retain their unmethylated form. As such, administration of a CpG adjuvant cloned into plasmid vectors would be simultaneous with the administration of a plasmid DNA vaccine. Alternatively, a CpG adjuvant in the form of free oligonucleotides may be administered before, during or after the administration of a plasmid DNA vaccine. Oligonucleotides having CpG motifs are modified at their phosphodiester linkages for stability purposes. For example, phosphodiester bonds in an oligonucleotide may be replaced by phosphorothioate linkages. DNA oligonucleotides containing unmethylated CgG dinucleotides are currently in phase I human trials. One note of caution is that the phosphorothioate oligonucleotide backbone, while essential for nuclease resistance, also confers a long half life and the long-term effects of maintaining these modified compounds in the body are yet to be determined.

The delivery system referred to as ISCOM contains the adjuvant saponin. Crude saponins are toxic, and much effort has gone towards purifying a less toxic saponin fraction which still retains the adjuvant properties. Results with a semi-purified fraction termed Quil A have been inconsistent, with differing levels of toxicity observed with different preparations. ISCOMs have now progressed to phase I and II of human trials, so the long term effects of these compounds remain to be seen (Sjolander et al., 1998). An exhaustive list of adjuvants are also described in Stewart-Tull, 1994.

Other immunomodulatory compounds have been proposed, including 8-bromoguanosine and ganglioside GM2 (Goodman, 1983; Livingston, 1995; Scheuer et al., 1985). Synthetic guanine nucleosides derivatized at either the C8 or at both N7 and C8 positions of the guanine base have been shown to possess some immunostimulatory and immunomodulatory properties (Goodman and Goodman, 1994; Reitz et al., 1994). None of these have yet been determined to possess the necessary characteristics of stability, safety and efficacy for clinical use as immune adjuvants in humans.

In summary, it appears that current adjuvant technology is still limited, as reflected by the fact that alum is the only FDA-approved human vaccine adjuvant.

SUMMARY OF THE INVENTION

The present invention overcomes the limitations of the prior art. The inventor has shown that two bacterial nucleotides, guanosine tetraphosphate (ppGpp) and guanosine pentaphosphate (pppGpp), can modulate the host immune system to mount a rapid immune response against a specific antigen. Co-administration of an antigen, alum, ppGpp, pppGpp or a mixture of ppGpp and pppGpp dramatically decreases the time required to elicit an immune response against the antigen. These may be co-administered as follows; 1) antigen and ppGpp; or antigen and pppGpp; or antigen and a mixture of ppGpp and pppGpp; 2) or antigen and ppGpp and alum; or antigen and pppGpp and alum; or antigen and a mixture of ppGpp and pppGpp and alum. It is expected that these and related agents may have broad use as adjuvants, as stimulants of the innate immune response, and as modifiers of the character of an immune response.

The bacterial nucleotides guanosine tetra- and pentaphosphate have never been tested as immunologic adjuvants. The present invention demonstrates that these compounds have an immunomodulatory effect in a mouse host when co-administered with an antigen in the presence of alum. An unexpected and desirable feature of the immune response is the increased kinetic rate of antibody elicitation as compared with standard alum adjuvant. Given that guanosine tetra- and pentaphosphate are small mononucleotides, it is likely that they exert their immunomodulatory effects by macrophage activation rather than by acting as repository adjuvants. The mechanism by which (p)ppGpp exerts an immunomodulatory effect is not yet fully understood.

The dramatic increase in the kinetic response that was observed in this study indicates that (p)ppGpp may be affecting the immune system in a way that differs from other adjuvants. To date, the main use of adjuvants has been to improve the magnitude of antibody responses (immunostimulatory effect). The identification of (p)ppGpp as a kinetic modulator of immune response (immunomodulatory effect) could have profound effects in the field of vaccinology. This novel and unexpected effect of (p)ppGpp would allow its use as a co-adjuvant, in combination with adjuvants that act by a different mechanism. It is contemplated that the nucleotides of this invention may be used in compositions that can modulate immune responses, in addition to any other adjuvant. An exhaustive list of existing adjuvants is described in Stewart-Tull, 1994, and can be found by one of ordinary skill in the art.

The invention provides a composition comprising a nucleotide that is capable of modulating the host immune system. The nucleotides of the invention modulate the immune system by altering the kinetics of response of the host immune system. In preferred embodiments, the nucleotides are guanosine tetraphosphate (ppGpp), guanosine pentaphosphate (pppGpp), or a mixture of ppGpp and pppGpp. In particular embodiments, administration of compositions comprising one or more of these nucleotides provides a more rapid response of the host immune system to antigens.

In another aspect of the invention, the composition further comprises alum. In certain embodiments of the invention, the composition further comprises an antigen.

The skilled artisan will realize that ppGpp and pppGpp may be chemically modified to enhance their stability and/or efficacy. Such modified nucleotides may still be used within the scope of the present invention. In non-limiting embodiments, labile phosphodiester or phosphoester linkages may be replaced with more stable linkages, such as phosphorothioate or thioester linkages. In certain embodiments, the nucleotides comprise a guanine residue. In preferred embodiments, the guanine residue is not chemically modified or otherwise substituted.

A further aspect of the invention comprises the administration of a nucleotide adjuvant. In one embodiment of the invention, the nucleotide adjuvant comprises guanosine tetraphosphate (ppGpp). In another embodiment of the invention, the nucleotide adjuvant comprises guanosine pentaphosphate (pppGpp). In still another embodiment of the invention, the adjuvant comprises a mixture of guanosine tetraphosphate and guanosine pentaphosphate.

Another further aspect of the invention comprises the administration of a nucleotide adjuvant in combination with an antigen. In one embodiment of the invention, the adjuvant is administered before administration of the antigen. In yet another embodiment of the invention, the adjuvant is administered after administration of the antigen. In still another embodiment of the invention, the adjuvant is administered in conjunction or substantially simultaneously with the antigen.

The invention further provides a method of producing antibodies by administering a nucleotide adjuvant. In one aspect of the invention, the nucleotide adjuvant comprises ppGpp. In another aspect of the invention, the nucleotide adjuvant comprises pppGpp. In a further embodiment of the invention the nucleotide adjuvant, comprises a mixture of guanosine tetraphosphate and guanosine pentaphosphate.

In one aspect of the invention, the method of producing antibodies further comprises administration of alum. In a further embodiment of the invention, the method of producing antibodies further comprises the administration of an antigen. In one other embodiment of the invention, the method of producing antibodies comprises administration of the adjuvant before administration of the antigen. In still another embodiment of the invention, the method of producing antibodies comprises administration of the adjuvant after administration of the antigen. In yet another embodiment of the invention, the method of producing antibodies comprises administration of the adjuvant in conjunction or substantially simultaneously with the antigen.

The invention also provides an antibody produced by the method of administering a nucleotide adjuvant. In one aspect of the invention, the nucleotide adjuvant comprises guanosine tetraphosphate (ppGpp). In another aspect of the invention, the nucleotide adjuvant comprises guanosine pentaphosphate (pppGpp). In a further embodiment of the invention, the nucleotide adjuvant comprises a mixture of guanosine tetraphosphate and guanosine pentaphosphate.

In another embodiment of the invention, the antibody is produced by further administering alum. In certain embodiments of the invention, the antibody is produced by further administration of an antigen. In a related embodiment of the invention, the antibody is produced by further administration of the adjuvant before administration of the antigen. In another related embodiment of the invention, the antibody is produced by further administration of the adjuvant after administration of the antigen. In yet another related embodiment of the invention, the antibody is produced by further administration of the adjuvant in conjunction or substantially simultaneously with the antigen.

In preferred embodiments, the pharmaceutical formulations suitable for administration of the nucleotides and adjuvants developed in this invention are described. Pharmaceutical formulations for different vaccine types that may be used in the present invention are described. Preferred modes of delivery of the nucleotides, adjuvants and vaccines are also described.

Following long-standing patent law convention, the words "a" and "an" mean "one or more" in this specification including claims.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Kinetics and magnitude of humoral response in mice. BALB/c mice (n=5) were immunized against HBsAg by i.m. injection of 1 $\mu$g of recombinant HBsAg protein, which was given alone (crosses); or coadministered with alum (25 $\mu$g $Al^{3+}$/$\mu$g HBsAg) (triangles); with (p)ppGpp (25 $\mu$g each of ppGpp and pppGpp) (open circles); or with alum plus (p)ppGpp (closed circles). Each point represents the group mean (n=5) for titers of anti-HBsAg total IgG as determined by two to four separate ELISA assays, each performed in triplicate. Titers were calculated from an anti-HBsAg standard curve generated with a monoclonal IgG antibody against HBsAg. Vertical lines represent the group standard errors of the mean (SEM).

FIG. 3A. Titrating effect of ppGpp on specific humoral response in mice. BALB/c mice (n=4) were immunized against HBsAg by i.m. injection of 1 μg of recombinant HBsAg protein. HBsAg was given alone. Group mean titers were calculated as described in the legend to FIG. 2. Vertical lines represent the group SEMs.

FIG. 3B. Titrating effect of ppGpp on specific humoral response in mice. BALB/c mice (n=4) were immunized against HBsAg by i.m. injection of 1 μg of recombinant HBsAg protein. HBsAg was given with alum. Group mean titers were calculated as described in the legend to FIG. 2. Vertical lines represent the group SEMs.

FIG. 3C. Titrating effect of ppGpp on specific humoral response in mice. BALB/c mice (n=4) were immunized against HBsAg by i.m. injection of 1 μg of recombinant HBsAg protein. HBsAg was given with alum plus 2 μg (3.6 nmol) ppGpp. Group mean titers were calculated as described in the legend to FIG. 2. Vertical lines represent the group SEMs.

FIG. 3D. Titrating effect of ppGpp on specific humoral response in mice. BALB/c mice (n=4) were immunized against HBsAg by i.m. injection of 1 μg of recombinant HBsAg protein. HBsAg was given with alum plus 10 μg (18 nmol) ppGpp. Group mean titers were calculated as described in the legend to FIG. 2. Vertical lines represent the group SEMs.

FIG. 3E. Titrating effect of ppGpp on specific humoral response in mice. BALB/c mice (n=4) were immunized against HBsAg by i.m. injection of 1 μg of recombinant HBsAg protein. HBsAg was given with alum plus 50 μg (90 nmol) ppGpp. Group mean titers were calculated as described in the legend to FIG. 2. Vertical lines represent the group SEMs.

FIG. 3F. Titrating effect of ppGpp on specific humoral response in mice. BALB/c mice (n=4) were immunized against HBsAg by i.m. injection of 1 μg of recombinant HBsAg protein. HBsAg was given with alum plus 250 μg (450 nmol) ppGpp. Group mean titers were calculated as described in the legend to FIG. 2. Vertical lines represent the group SEMs.

FIG. 4A. Effect of guanine compounds on specific humoral response in mice. BALB/c mice (n=5) immunized against HBsAg by i.m. injection of 1 μg of recombinant HBsAg protein with alum adjuvant. Group mean titers were calculated as described in the legend to FIG. 2. Vertical lines represent the group SEMs.

FIG. 4B. Effect of guanine compounds on specific humoral response in mice. BALB/c mice (n=5) immunized against HBsAg by i.m. injection of 1 μg of recombinant HBsAg protein with alum plus 10 μg (18 nmol) ppGpp. Group mean titers were calculated as described in the legend to FIG. 2. Vertical lines represent the group SEMs.

FIG. 4C. Effect of guanine compounds on specific humoral response in mice. BALB/c mice (n=5) immunized against HBsAg by i.m. injection of 1 μg of recombinant HBsAg protein with alum plus 10 μg (18 nmol) pppGpp. Group mean titers were calculated as described in the legend to FIG. 2. Vertical lines represent the group SEMs.

FIG. 4D. Effect of guanine compounds on specific humoral response in mice. BALB/c mice (n=5) immunized against HBsAg by i.m. injection of 1 μg of recombinant HBsAg protein with alum plus 5 μg (9 nmol) ppGpp and 5 μg (9 nmol) pppGpp. Group mean titers were calculated as described in the legend to FIG. 2. Vertical lines represent the group SEMs.

FIG. 4E. Effect of guanine compounds on specific humoral response in mice. BALB/c mice (n=5) immunized against HBsAg by i.m. injection of 1 μg of recombinant HBsAg protein with alum plus 10 μg (18 nmol) GTP. Group mean titers were calculated as described in the legend to FIG. 2. Vertical lines represent the group SEMs.

FIG. 5. Comparison of adjuvant effects of ppGpp vs. unmethylated CpG oligonucleotide. The humoral response in BALB/c mice (n=4) immunized against HBsAg was compared for ppGpp and CpG. HBsAg was given with alum (solid triangles), with alum plus 1 μg ppGpp (solid circles) or alum plus 10 μg oligonucleotide 1826 (solid diamonds), and the humoral response was measured by ELISA. Group mean titers (n=4) were calculated as described in the legend to FIG. 2. The predicted humoral response for HBsAg delivered with alum plus 10 μg of the unmodified equivalent of oligonucleotide 1826 is shown for comparison (open diamonds, dotted line).

DESCRIPTION OF ILLUSTRATIVE EMBODIMENTS

A. The Present Invention

The inventor has shown that two simple bacterial nucleotides, guanosine tetraphosphate (ppGpp) and guanosine pentaphosphate (pppGpp), can modulate the host immune system to mount a rapid immune response against a specific antigen. Specifically, co-administration of an antigen, alum and ppGpp or a mixture of ppGpp and pppGpp dramatically decreases the time required to elicit an immune response against the antigen. It is expected that these and related agents may have broad use as adjuvants, as stimulants of the innate immune response, and as modifiers of the character of an immune response.

Guanosine tetra- and pentaphosphate or simple derivatives of them have the potential to be used clinically as adjuvants in humans and animals for immunotherapy, and for prophylactic and therapeutic vaccination against infectious diseases. These reagents could also be used to modify a deleterious immune response, for example to shift it from a Th2 allergy response to a more Th1 response (see definitions of Th1 and Th2 at the end of this section). Based on the experience with CpG oligonucleotides it is likely that these agents would also produce a protective stimulation of the innate response that would protect against a wide variety of infections. In addition, they can greatly facilitate experimental animal studies and trials by greatly decreasing the length of time that is required to raise an immune response.

Another great advantage of using guanosine tetra- and pentaphosphate as adjuvants is that they can be readily synthesized at high levels in the laboratory either biologically, using isolated bacterial ribosomes for synthesis, or chemically, using standard techniques. Furthermore, production methodology can be readily standardized to ensure consistent quality control. In fact, at one stage when many people were investigating the physiological role of (p)ppGpp in bacteria, these compounds were commercially produced. However, since the interest level in studying these compounds has subsequently reduced, they are no longer commercially available. It is however possible to chemically synthesize (p)ppGpp compounds. More importantly, it is also possible to synthesize modified forms of the both ppGpp and pppGpp which are more stable to hydrolysis, and thus less susceptible to degradation by nucleases and/or pyrophosphatases.

Some Definitions Used in this Application are

"Adjuvant" is used to describe a substance incorporated into or injected simultaneously with antigen which potentiates the immune response, either specifically or nonspecifically.

"Antigen Presenting Cells", or "APC's" include known APC's such as Langerhans cells, veiled cells of afferent lymphatics, dendritic cells and interdigitating cells of lymphoid organs. The definition also includes mononuclear cells such as (1) lymphocytes and macrophages which take up and express polynucleotides in skin and (2) mononuclear cells. The most important of these with respect to the present invention are those APC's which are known to be present in high numbers in epithelia and thymus dependent areas of the lymphoid tissues, including epidermis and the squamous mucosal epithelia of the buccal mucosa, vagina, cervix and esophagus.

"Host" refers to the recipient of the therapy to be practiced according to the invention. The host may be any vertebrate, but will preferably be a mammal. If a mammal, the host will preferably be a human, a domestic livestock or a pet animal or an experimental animal.

"Th1 Response(s)" refers to a cellular immune response that is induced preferentially by antigens that bind to and activate certain APC's; i.e., macrophages and dendritic cells.

"Th2 Response(s)" refers to a humoral immune response that is induced preferentially by antigens that bind to and activate the B-cells to produce antibodies.

B. Adjuvant Development

This invention shows that pppGpp and ppGpp have immunomodulatory properties which are associated with immunologic adjuvants. The term adjuvant is widely used to describe a substance incorporated into or injected simultaneously with antigen which potentiates the immune response, either specifically or nonspecifically. To date, adjuvant development has been largely an empirical exercise, since the mechanisms by which adjuvants act or what factors influence their efficacy are not widely understood in the art. Nevertheless, a great many materials have been shown to have adjuvant activity (an exhaustive list of adjuvants and methods of preparing them are described in Stewart-Tull, 1994, which is incorporated herein by reference), eliciting responses by diverse modes of action, which can be broadly classified into two categories (Roitt, 1994; Ada, 1993; Roitt et al., 1996; Stewart-Tull, 1994):

1. Depot Effect: Repository adjuvants act by counteracting rapid dispersal of antigen upon injection, thus providing a long-lived reservoir of antigen. The most common adjuvants of this type used in man are aluminum compounds including. aluminum salts (hydroxide and phosphate, commonly referred to as alum). These are essentially hydrophilic suspensions on which the antigen is adsorbed. Alum was first used as an adjuvant more than 75 years ago and is still the only preparation approved by regulatory authorities for human vaccines. Other repository adjuvants include Freund's incomplete adjuvant, in which the antigen is incorporated in the aqueous phase of a stabilized water in paraffin oil emulsion, liposomes, and immune-stimulating complexes called ISCOMs (which are comprised of saponin, cholesterol, phospholipid and immunogen).

2. Macrophage Activation: Virtually all adjuvants stimulate macrophages which are thought to act by improving immunogenicity through an increase in the concentration of processed antigen on their surface and the efficiency of its presentation to lymphocytes. Bacterial products such as endotoxin, pertussis toxin, and lipid A (derived from Gram negative lipopolysaccharide), are thought to act mainly by stimulating the formation of the appropriate cytokines. In fact, modulatory cytokines such as GM-CSF, IL-1 and IL-2 themselves have been shown to be effective adjuvants.

Arguably the "gold standard" for experimental work, Freund's complete adjuvant, is made from the incomplete adjuvant (see above) by addition of killed mycobacteria. Bacterial DNA alone is a powerful adjuvant owing to the presence of unmethylated CpG dinucleotides, eliciting immunostimulatory effects which include upregulation of co-stimulatory molecules on antigen-presenting cells (APC), and induced secretion of immunoregulatory cytokines (Allison and Byars, 1991). Natural bacterial DNA containing unmethylated CpG dinucleotides, and synthetic bacterial containing DNA CpG repeats are B-cell mitogens, dictating a Th1 bias to the developing adaptive immune response. In addition, antigen-receptor occupancy augments B-cell response and controls T-cell responsiveness to the CpG repeats (Lipford et al., 1998). ISCOMs, described above as repository adjuvants, also appear to promote a broad immune response by simultaneously promoting high levels of antibody as well as strong T cell responses.

C. ppGpp and pppGpp

Figure 1:
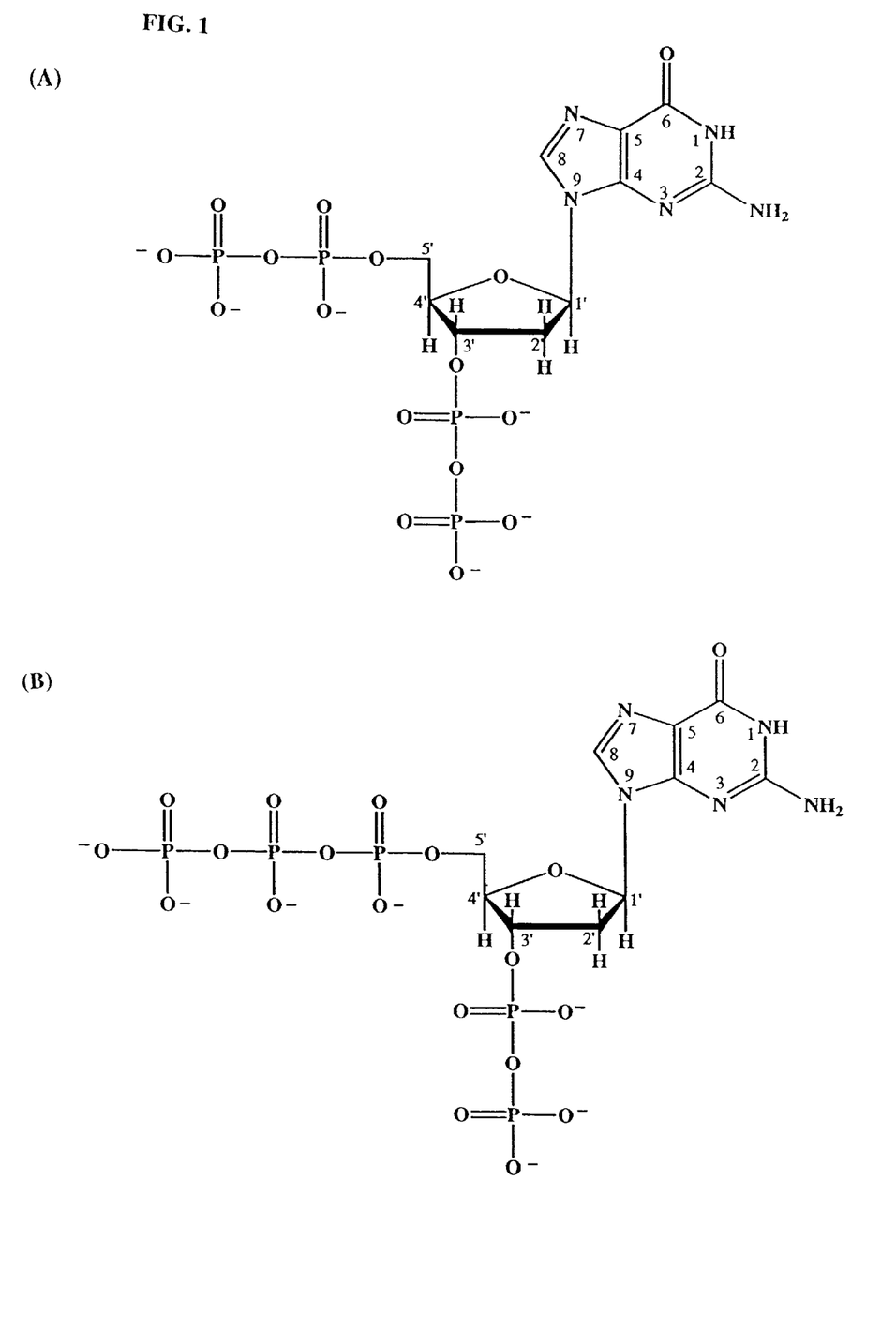
FIG. 1A. Bacterial nucleotides responsible for the stringent control of ribosomal RNA and transfer RNA synthesis. Guanosine 5'-diphosphate 2'(3')-diphosphate (ppGpp; also called guanosine tetraphosphate or magic spot I).
FIG. 1B. Bacterial nucleotides responsible for the stringent control of ribosomal RNA and transfer RNA synthesis. Guanosine 5'-triphosphate 2'(3')-diphosphate (pppGpp; also called guanosine pentaphosphate or magic spot II).

When bacteria are starved under culture for amino acids or carbon compounds, they turn on the "stringent response" during which the nucleotides ppGpp and pppGpp are produced (Cashel, 1975; Gallant, 1979). The chemical structures of these compounds is shown in FIG. 1. When a bacterial pathogen invades a mammalian host, it typically encounters a nutritionally limited environment. Given that this situation is physiologically similar to that which leads to the stringent response in culture, it is likely that (p)ppGpp is produced during the early stages of a bacterial infection. To date, the inventor knows of no one that has investigated this possibility, since studies of (p)ppGpp have been carried out with bacteria grown in culture. The inventor was the first to study the biological effects of introducing (p)ppGpp into a mammalian host, and specifically to test immune effects.

In recent years, it has come to light that a number of bacterial and viral compounds can activate and/or modulate the mammalian immune system in a nonspecific manner (Marrack and Kappler, 1994; Heeg et al., 1998). The immune system has evolved to respond to various "foreign" compounds. The inventor evaluated the bacterial nucleotides (p)ppGpp which are produced during the early stages of infection, and are detected by a sensing mechanism within the host which signals the immune system to mount an immune response. It was found that (p)ppGpp can dramatically modulate the immune response when co-administered with an antigen (hepatitis B surface antigen) into a mouse host.

The results described herein are the first to shown that (p)ppGpp can act as a biological response modifier in a mammalian system. Moreover, this is the first demonstration that a simple bacterial secondary metabolite, (p)ppGpp, can modulate the host immune system to mount a rapid immune response against a specific antigen. The skilled artisan will realize that guanosine tetra- and pentaphosphate may be used clinically as adjuvants in humans and animals for immunotherapy, and for prophylactic and therapeutic vaccination against infectious and non-infectious diseases in animals and humans. ppGpp and or pppGpp may be administered by themselves or in combination with a subunit, live/attenuated, DNA-based or other forms of vaccine (described in Examples). Prophylactic application will be most critical during infectious outbreaks, when a rapid immune response to a vaccine is critical.

An important nonclinical application of (p)ppGpp adjuvant is for animal research, since a significant amount of time is usually required for animals to mount an immune response against a given antigen. Reduction of this time by the co-administration of (p)ppGpp will reduce the amount of time required to obtain experimental data and will reduce costs due to shorter time required for animal housing.

Several general conclusions can be drawn from the results described herein. Guanosine tetra- and pentaphosphate are immunomodulatory molecules. They act as adjuvants when co-administered with an antigen in the presence of alum, resulting in accelerated development (by 2 to 4 wk) of a specific immune response when compared with standard alum adjuvant alone. The speed with which an immune response is elicited with ppGpp is at least as fast as that observed with a nuclease-resistant oligonucleotide containing unmethylated CpG's, which is known to be a very strong adjuvant. Although ppGpp and pppGpp affect the kinetics of the immune response, they do not appear to affect the magnitude of the humoral response when compared to injection of antigen with alum alone.

A novel and unexpected result was that the mixture of ppGpp and pppGpp was substantially more effective than either compound alone, suggesting that ppGpp and pppGpp may be modulating the immune system through different mechanisms to give a synergistic response. Together, these results demonstrate the novelty and great utility of the (p)ppGpp adjuvant.

The fact that (p)ppGpp acts synergistically with alum to give a much more rapid immune response, indicates that this simple application alone is a great improvement upon current technology. A very important and unique advantage that (p)ppGpp has over other adjuvants is the fact that it greatly affects the kinetics of the immune response, giving rise to immunity at a significantly earlier time than standard alum adjuvant. The rapidity with which an immune response can be mounted is extremely important (as outlined above). To this end (p)ppGpp provides a means to accelerate the immune response, and to develop a rapid protection against infectious agents. Given that (p)ppGpp has immunomodulatory properties, it is possible that other aspects of immunity may also be positively affected, potentially including magnitude and longevity.

In addition to their immunological benefits, guanosine tetra- and pentaphosphate have the distinct advantage of being natural, small and structurally simple molecules. Based on their structures, which are similar to those of guanosine di- and triphosphate (GDP and GTP, respectively) which are essential and found in relatively high concentrations in all living cells, including mammalian cells, they should be fairly innocuous from a chemical and physiological point of view. It is encouraging that no signs of toxicity were observed, even at levels as high as 250 µg ppGpp per mouse.

Furthermore, ppGpp and pppGpp molecules do not generate an antibody response against themselves. Attempts to produce anti-ppGpp antibodies in mice for analytical purposes did not result in antibody production unless ppGpp was linked to a hapten, showing that (p)ppGpp molecules are too small to elicit an immune response. It is well known in the art of antigens and antigen presentation that very small molecules do not generate an antibody response against themselves, for example, small molecules such as haptens have to be linked to a carrier protein in order to generate an antibody response (see Robinson, A., 1996, Chapter 8, pp. 111–125).

D. Chemically Modified Analogs of (p)ppGpp

In certain embodiments, the structure of (p)ppGpp may be chemically modified, for example to enhance its stability in vivo. Non-limiting examples of nucleotide modifications that may be used within the scope of the instant invention are provided below. The relevant portions of the cited U.S. patent applications are incorporated herein by reference.

U.S. Pat. No. 5,714,606 concerns a modified nucleotide linkage wherein a 3'-position oxygen of the linkage is replaced by a carbon. U.S. Pat. No. 5,672,697 concerns nucleotides containing one or more 5' methylene phosphonate linkages. U.S. Pat. No. 5,470,967 concerns Nucleotides comprising at least one sulfamate or sulfamide linkage. Each of these modifications results in enhanced resistance to nuclease activity, that would be expected to increase the stability of (p)ppGpp in vivo.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Antigenic Regions for Vaccination and Types of Vaccines

The goal of the present invention concerning development of novel and effective adjuvants is to provide preventive therapeutics to a host (animal or human) with a vaccine. The vaccine may be a subunit vaccine such as but not limited to the HBsAg used in several of the studies described in this application; a live/attenuated vaccine; or even a gene construct encoding an antigen which will be a specific or desired protein, polypeptide or peptide.

One of skill in the art will recognize that there are many vaccines that can be used with regard to this invention and some examples follow.

A. Live/Attenuated Vaccines

The present invention is advantageously employed with viruses or bacterial pathogens that are live but have been attenuated so that they do not cause disease in the host vaccinated. Typically resistance to viral or bacterial pathogens is mediated by the development of an immune response to the genes coding for viral surface antigens.

Attenuation can be achieved in several ways; by transfer of attenuating genes from an attenuated donor virus to a replicated isolate or a reasserted virus according to known methods (see, e.g., Murphy, 1993); cold attenuation; or attenuated by mutations introduced into non-coding and coding regions of the genome. Such attenuating mutations can also be introduced into genes other than the surface antigen genes, e.g., the PB2 polymerase gene (Subbarao et al., 1993).

It is preferred that such attenuated pathogens maintain the genes from the original infectious pathogens that encode antigenic determinants substantially similar to those of the original clinical isolates. This is because the purpose of the attenuated vaccine is to provide substantially the same antigenicity as the original clinical isolate of the pathogen, while at the same time lacking infectivity to the degree that the vaccine causes minimal chance of inducing a serious pathogenic condition in the vaccinated mammal.

Several live/attenuated viral vaccines have been developed and one of skill in the art will appreciate the possibility of using any vaccine of this type in combination with the nucleotide adjuvants described in the present invention. Several live/attenuated bacterial pathogens are also available and the skilled artisan will recognize the usage of any of these vaccines with in conjunction with the adjuvants developed in the present invention.

B. Subunit Vaccines

Subunit vaccines include antigens which are immunogenic in compositions and mediate an immune response and include protein subunits of microbial pathogens, bacteria, viruses, proteins, glycoproteins lipoproteins, peptides, glycopeptides, lipopeptides, toxoids, carbohydrates, and tumor-specific antigens. Mixtures of two or more antigens may be employed.

Such peptides, glycopeptides or lipopeptides may include an amino acid sequence corresponding to an antigenic determinant of HIV, Rubella virus, Respiratory Syncytial Virus, Bordetella pertussis, Haemophilus influenzae or Streptococcus pneumoniae, including their specific synthetic peptides or a functional analog thereof. The toxoid may be a pertussis toxoid while the protein may be influenza hemagglutinin or a parainfluenza virus subunit, such as the HN or F proteins of PIV-3.

C. DNA-based Vaccines

While the subunit vaccines and the live/attenuated vaccines are delivered directly, for the genetic or DNA-based vaccines a preferred embodiment for delivery involves providing a nucleic acid encoding a specific or desired protein, polypeptide or peptide to the cell. Following this provision, the proteinaceous composition is synthesized by the transcriptional and translational machinery of the cell, as well as any that may be provided by the expression construct.

In certain embodiments of the invention, the nucleic acid encoding the antigen may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed. A preferred embodiment of delivery for this invention is using the gene gun and or intramuscular injection. However, other well known methods of DNA-based vaccine delivery known in the art are also envisioned to be used.

Example 2

Pharmaceuticals and Modes of Administration

Aqueous compositions of the present invention comprising effective amounts of the nucleotides, adjuvants, antigens, antibodies, DNA sequences, or other compounds of the invention, may be dissolved or dispersed in a pharmaceutically acceptable carrier or medium to form preventive or therapeutic formulations of the invention.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds of the present invention, will generally be formulated for parenteral administration, e.g., formulated for injection via the intravenous (i.v.), intramuscular (i.m.), subcutaneous (s.c.), intralesional (i.l.), or even intraperitoneal (i.p.) routes. Genetic vaccines have several modes of delivery well known to those of ordinary skill in the art. Among these methods intramuscular injection or delivery by gene gun are preferred modes. The preparation of an aqueous composition that contains an adjuvant, an antigen, an antibody, a DNA sequence or other agent as an active component or ingredient will be known to those of skill in the art in light of the present disclosure. Typically, such compositions can be prepared as injectibles, either as liquid solutions or suspensions; solid forms suitable for using to prepare solutions or suspensions upon the addition of a liquid prior to injection can also be prepared; and the preparations can also be emulsified.

The pharmaceutical forms suitable for injectible use include sterile aqueous solutions or dispersions; formulations including sesame oil, peanut oil or aqueous propylene glycol; and sterile powders for the extemporaneous preparation of sterile injectible solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free acid or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Formulations of neutral or salt forms are also provided. Pharmaceutically acceptable salts, include the salts derived by addition of inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectible compositions can be brought about by the use in the compositions of agents delaying absorption, for example, aluminum monostearate and gelatin.

Sterile injectible solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectible solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for local injection also is contemplated.

Upon formulation, solutions will be administered in a manner compatible with the dosage formulation and in such amount as is preventively or therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In other embodiments, wherein the vaccines are directed toward cancer-therapies direct intratumoral injection is contemplated. Alternatively, the tumor may be infused or perfused with the therapeutic compounds using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is also contemplated.

In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated or diagnosed. The person responsible for administration will, in any event, determine the appropriate dose for the individual subject.

Example 3

Preparation of Nucleotides

The guanosine tetra- and penta-phosphates may be purified as described in Cashel, 1974. Briefly, this involves batch (p)ppGpp synthesis from purified bacterial ribosomes, lithium salt precipitation of nucleotides, and filtration through a QAE-sephadex column, using lithium chloride to elute. Concentrations may be assessed by measuring absorbance at 252 nm, and purity by thin layer chromatography on PEI-cellulose. The nucleotides may be lyophilized for long term storage and dissolved in endotoxin-free T.E. (pH 8.0) at a concentration of 25 $\mu g/\mu l$ immediately prior to use. Other methods for the synthesis of the nucleotides of this invention are described in Example 11 below.

Example 4

Immunization of Mice Against HBsAg

Immunization with HBsAg was conducted on groups of (n=4 or 5) 6- to 8-week old female BALB/c mice (Harlan) as described in, Davis et al., 1996. Each solution contained 1 $\mu g$ recombinant HBsAg protein (ayw subtype; Genzyme) in a total volume of 50 $\mu l$, and 25 $\mu l$ of each antigen solution was injected into both the left and right tibialis anterior muscles. Control groups received HBsAg in PBS (pH7.4) or HBsAg with 2.5 $\mu l$ of 2% aluminum hydroxide, $Al_2O_3$, also known as alum (Alhydrogel, Accurate Chemical and Scientific Corp., N.Y.) to give 25 $\mu g$ $Al^{3+}/\mu g$ HBsAg. This is the same ratio as used in the commercial hepatitis B vaccines (Davis et al., 1996). Experimental groups in Trial 1 received HBsAg plus 25 $\mu g$ of guanosine tetraphosphate and 25 $\mu g$ of guanosine pentaphosphate, both with and without alum. Experimental groups in Trial 2 received HBsAg and alum plus 2 $\mu g$, 10 $\mu g$, 50 $\mu g$ and 250 $\mu g$ of guanosine tetraphosphate. One experimental control group received alum plus 10 $\mu g$ of an oligonucleotide (oligo 1826, also referred to as a CpG ODN) which contains unmethylated CpG dinucleotides. (Oligonucleotide 1826, previously described in Davis et al., 1996, contains a nuclease-resistant phosphorothioate modified backbone). All component solutions were added at the same time, vortexed briefly, and left on ice for 30 minutes prior to injection to allow sufficient time for the antigen to adsorb to alum.

Example 5

ELISA Protocol

The ELISA method was used to evaluate the immune response to a combination of ppGpp and pppGpp and the immune response to ppGpp alone. Kinetics and magnitude of the immune response generated by the nucleotide ppGpp versus an oligonucleotide containing CpG were also determined from the data generated by ELISA. For the isotyping ELISAs the Immunopure Monoclonal Antibody Isotyping Kit I (HRP/ABTS) from Pierce was modified and used. The kit is designed for monoclonal AB's and not for sera, hence the inventor carried out some modifications.

Some general methods for the ELISA method are described. One of ordinary skill in the art will appreciate that any one of these modes or modifications may be used in the practice of the present invention.

In one exemplary ELISA, antibodies binding to the encoded proteins of the invention are immobilized onto a selected surface exhibiting protein affinity, such as a well in a polystyrene microtiter plate. Then, a test composition suspected of containing the antigen, such as but not limited to a clinical sample, is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA". Detection also may be achieved by the addition of a second antibody, followed by the addition of a third antibody that has binding affinity for the second antibody, with the third antibody being linked to a detectable label.

In another exemplary ELISA, the samples suspected of containing the antigen, are immobilized onto the well surface and then contacted with the antibodies of the invention. After binding and washing to remove non-specifically bound immunecomplexes, the bound antibody is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the antigenic protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control human cancer and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 h at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

In other embodiments, solution-phase competition ELISA is also contemplated. Solution phase ELISA involves attachment of the antigen to a bead, for example a magnetic bead. The bead is then incubated with sera from human and animal origin. After a suitable incubation period to allow for specific interactions to occur, the beads are washed. The specific type of antibody is the detected with an antibody indicator conjugate. The beads are washed and sorted. This complex is the read on an appropriate instrument (fluorescent, electroluminescent, spectrophotometer, depending on the conjugating moiety). The level of antibody binding can thus by quantitated and is directly related to the amount of signal present.

Example 6

Assays to Determine the Mechanism of the Immune Response Generated

A. Assay of Humoral Immune Response

For measuring humoral response to HBsAg blood was recovered from mice by tail vein bleeds at various times after immunization. The blood was clotted at room temperature for >2 hours, and centrifuged twice at 13 krpm for 10 minutes to separate the serum. Antibodies specific to HBsAg were detected by ELISA, and were quantified relative to a monoclonal antibody against HBsAg (IgG1, $10^{10}$ affinity constant, ad+ay; Genzyme). A solid phase of recombinant HBsAg protein (100 μl of 1 μg/ml per well, overnight at 4° C.) was used to capture anti-HBsAg in the plasma (overnight at 4° C.), which was then detected with HRP-conjugated rabbit anti-mouse IgG+IgM. (1:10,000 in PBS/0.1% Tween/2% BSA; 100 μl per well; Pierce), followed by the sequential addition of 3 3',5,5'-tetramethylbenzidine solution (50 μl/well, 10 minutes at room temperature; Calbiochem) and 0.25M HCl (50 μl/well). Absorbance was measured at 450 nm within 10 minutes of adding the final reagent. Anti-HB titers are expressed as group means +/−standard error (SE) of individual animals values, which are in turn averages of triplicate assays.

B. Assay of Cell-mediated Immune Response

In addition to the humoral immunity studies some of the mice can be sacrificed and tested for cellular immunity, primarily by CTL (cytotoxic T-lymphocyte) assay. CTL assays can be conducted to detect cell-mediated immune response stimulation in mice by administering antigen to which the host has been immunized. CTL can be generated by techniques known to those skilled in the art. CTL will then be harvested by ficoll/hypaque density gradient centrifugation and resuspended in suitable medium for use. In the CTL assay, antigen specific T-cells are detected by their ability to respond to antigen by their ability to lyse target cells.

The CytoTox 96® Non-Radioactive Cytotoxicity Assay kit from Promega to perform the lactate dehydrogenase (LDH) release assay can be used to measure the ability of antigen specific T-cells to release the enzyme. The CytoTox 96® Non-Radioactive Cytotoxicity Assay is a colorimetric assay. The CytoTox 96® Assay quantitatively measures lactate dehydrogenase (LDH), a stable cytosolic enzyme that is released upon cell lysis, in much the same way as $^{51}$Cr is released in radioactive assays. Released LDH in culture supernatants is measured with a 30-minute coupled enzymatic assay which results in the conversion of a tetrazolium salt (INT) into a red formazan product. The amount of color formed is proportional to the number of lysed cells. Visible wavelength absorbance data are collected using an ordinary 96 well plate reader. Methods for determination of LDH utilizing tetrazolium salts in conjunction with diaphorase or alternate electron acceptors have been used for several years and are known to those of ordinary skill in the art.

Alternately, the Cr release assay may be used as well. Here target cells, which are cells expressing the antigen of interest, are first incubated with $^{51}$Cr to aid the uptake of the radiolabel which binds to cellular proteins. Excess $^{51}$Cr is then washed out and the labeled target cells are then plated out. The $^{51}$Cr-labeled target cells are then co-cultured with the immunized CTL cells suitable medium in triplicate, in 96 well V-bottomed plates and cultured for 4–16 hours. Cytolysis can be determined by release of radioactive chromium from the target cells after incubation at 37° C. by counting the label released.

Example 7

Development of Delivery Systems

The delivery system used to administer (p)ppGpp may be optimized. To this end, alum adjuvant can be compared with relatively inert repository adjuvants such as mineral oil. One can also determine if the nature of the immunity elicited by (p)ppGpp can be biased towards a humoral or cellular response by the nature of the vehicle.

The inventor has used a plasmid carrying a gene for HBsAg described in Davis et al., 1993. Intramuscular injection was used to deliver 50 µg plasmid DNA either i) alone, ii) with alum (same amount as for the protein vaccine), iii) with alum plus 10 µg ppGpp, or iv) with alum plus 50 µg ppGpp. It is possible to test the same plasmid plus (p)ppGpp administered using the gene gun. In this case, the plasmid and (p)ppGpp can be coated onto gold particles, and these are "shot" into the ears of mice. In addition to testing the effect of (p)ppGpp on genetic vaccines, this gene gun approach can test whether the immunomodulatory effect is seen if the vaccine plus adjuvant go straight into a cell. As the intramuscular injection delivers the vaccine extracellularly and if (p)ppGpp interacts with/via a cell-surface receptor, it is possible that the adjuvant effect will not be seen with a gene gun. Thus, these studies will also shed light on the mechanism of the response.

In light of the fact that (p)ppGpp can synergistically interact with alum adjuvant to give an enhanced immune response, it is likely that (p)ppGpp can be combined with other adjuvants to yield similar results. For example, liposomes and ISCOMs may prove to be useful delivery systems to use in combination with (p)ppGpp, allowing one to take advantage of the different immunomodulatory properties of each compound. This combinatorial approach may also be advantageous in that would allow one to tailor a rapid immune response, using the delivery system (or co-adjuvant) to determine whether the response has a Th1 or Th2 bias, and using (p)ppGpp to facilitate the rapidity and level of this response.

Example 8

Determination of Longevity of the Humoral-Immune Response

A group of vaccinated mice can be monitored for anti-HBsAg antibody production, in order to determine the longevity of the (p)ppGpp/alum-induced humoral response relative to that of no adjuvant or alum alone. The preferred technique used to monitor the kinetics, magnitude and time course of the humoral response can be ELISA as described above.

Example 9

Use of ppGpp and pppGpp with Genetic Vaccines

The studies described in this application so far were carried out using a protein test antigen (HBsAg), which is a standard subunit vaccine. Studies with genetic vaccines can be performed to determine the efficacy of ppGpp and pppGpp as adjuvants when co-administered with the DNA-based vaccine. Previous sections describe the different types and methods of delivery of DNA-based vaccines.

Example 10

Synergistic Interactions Between CpG and (p)ppGpp

Any synergistic interaction between the CpG oligonucleotide and (p)ppGpp can be evaluated by co-injecting CpG and (p)ppGpp as a combined adjuvant. Again, ELISA and other methods described above can be used to determine the strength, kinetics and nature of the immune response generated. Briefly, the vaccination protocol described above for the HBsAg protein can be used. The groups tested may be as follows: HBsAg plus i) alum alone, ii) alum plus 10 µg ppGpp, iii) alum plus 10 µg CpG oligo 1826, iv) alum plus 10 µg ppGpp plus 10 µg CpG oligo 1826, v) alum plus 1 µg CpG oligo 1826, vi) alum plus 1 µg ppGpp plus 10 µg CpG oligo 1826. Results can be monitored by an ELISA.

Another subject investigation is the direct immunostimulatory effects of (p)ppGpp upon cultured dendritic cells (which are APC's).

Example 11

Obtaining ppGpp and pppGpp

A great advantage of using guanosine tetra- and pentaphosphate as adjuvants is that they can be readily synthesized at high levels in the laboratory either biologically, using isolated bacterial ribosomes for synthesis, or chemically, using standard techniques usually known to those of ordinary skill in the art. Furthermore, production methodology can be readily standardized to ensure consistent quality control.

A. Bacterial Ribosomes for Synthesis

Bacteria starved under culture for amino acids or carbon compounds turn on the "stringent response" during which the nucleotides ppGpp and pppGpp are produced (Cashel, 1975; Gallant, 1979). It is known that bacterial ribosomes are involved in the synthesis of ppGpp and pppGpp. Thus, harvesting bacterial ribosomes where the bacteria are initially subject to a nutritionally limited environment allows bacterial synthesis of ppGpp and pppGpp. This is followed by a suitable extraction procedure which involves batch pppGpp synthesis from purified bacterial ribosomes, precipitation of nucleotides using lithium salt, and filtration through a QAE-sephadex column, using lithium chloride to elute. Concentrations are assessed by measuring absorbance at 252 nm, and purity by thin layer chromatography on PEI-cellulose.

B. Chemical Synthesis

Chemically synthesis of ppGpp and pppGpp compounds is possible. In fact, at one stage when many people were investigating the physiological role of (p)ppGpp in bacteria, these compounds were commercially produced. However, since the interest level in studying these compounds has subsequently reduced, they are no longer commercially available. Based on the chemical structures, the method of chemical synthesis should be straightforward.

C. Analogs of ppGpp and pppGpp

More importantly, it is also possible to synthesize modified forms of the both ppGpp and pppGpp which are more stable to hydrolysis, and thus less susceptible to degradation by nucleases and/or pyrophosphatases.

In the case of CpG oligonucleotides, the stable, nuclease-resistant synthetic oligonucleotide (in which the phosphodiester backbone was replaced with a phosphorothioate backbone) was more than 2 orders of magnitude more effective than the unmodified form in immunological assays (Krieg et al., 1995). Therefore, the inventor contemplates that reasonable chemical modification of (p)ppGpp can increase the half-life and have a similar effect in increasing the immunomodulatory effect.

The skilled artisan will realize that methods are generally known in the art for chemically synthesizing modified versions of (p)ppGpp which are less susceptible to hydrolysis. Some of these are referred to above. However, the invention is not limited to those chemical modifications specifically incorporated by reference, but may also include other known modifications to increase the stability and half-life of (p)ppGpp in vivo. It is contemplated that a greater half-life in the mammalian host may lead to a faster and/or greater immune response.

Example 12

Immune Response to a Combination of ppGpp and pppGpp

Figure 2:
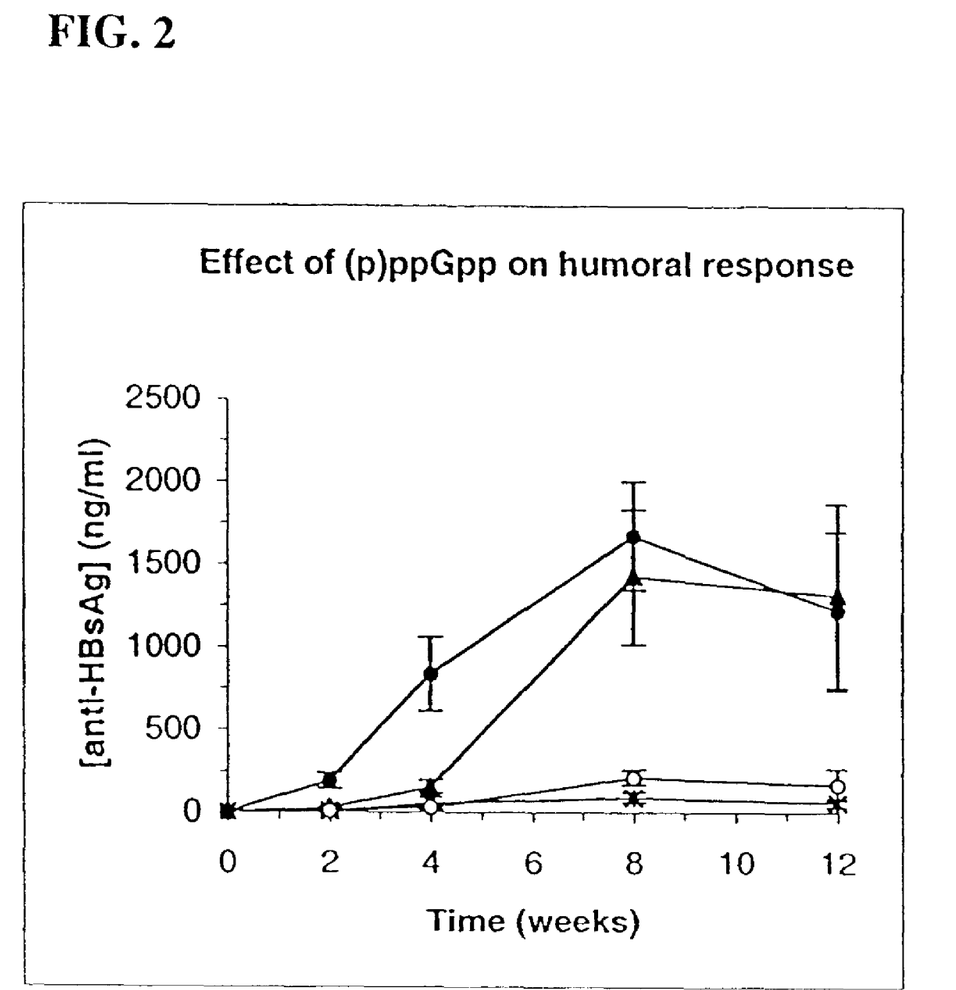

The effect of a mixture ("(p)ppGpp")of ppGpp and pppGpp on the generation of a specific immune response was tested (FIG. 2). BALB/C mice were immunized by intramuscular (i.m.) injection with 1 $\mu$g hepatitis B surface antigen (HBsAg) alone (crosses); HBsAg plus alum (a standard adjuvant; 25 $\mu$g $Al^{3+}$/$\mu$g HBsAg) (triangles); HBsAg plus 25 $\mu$g ppGpp and 25 $\mu$g ppGpp (open circles), or HBsAg plus alum, ppGpp and pppGpp (closed circles). The humoral (antibody) response against HBsAg was measured at various time points by ELISA (FIG. 2). Where alum was added, the antigen and/or (p)ppGpp were preadsorbed onto aluminum hydroxide (alum adjuvant) prior to injection.

Mice that received HBsAg protein alone attained low titers of anti-HBsAg antibodies, consistent with previous reports (FIG. 2, mean ELISA concentration of serum anti-HBsAg IgG of 90±30 ng/ml at 8 weeks post-immunization; Davis et al., 1998). Use of (p)ppGpp without alum did not significantly increase the humoral response.

Comparing the time course of the humoral response between mice receiving (p)ppGpp plus alum (closed circle) versus those receiving alum alone (crosses), it is clear that administration of (p)ppGpp shortened the humoral response time by approximately 2 to 4 weeks. Anti-HBsAg antibodies were significantly higher than control groups (alum alone) by 2 weeks after injection (FIG. 2, p=0.002). By 4 weeks after injection the (p)ppGpp plus alum group showed a 5-fold higher antibody titer than alum alone (FIG. 2, 832±224 ng/ml vs. 152±42 ng/ml, respectively). By 8 weeks after injection, there was no significant difference between HBsAg plus alum and HBsAg plus alum plus (p)ppGpp (FIG. 2).

The presence of (p)ppGpp dramatically changed the kinetics of the immune response, giving rise to significant anti-HBsAg antibody production at a much earlier stage after immunization. The maximum response observed was not significantly different in the presence or absence of (p)ppGpp (compare open circles vs. crosses, or closed circles vs. triangles) under these conditions. Thus, (p)ppGpp appears to exhibit a unique effect as an adjuvant by substantially shortening the time required for an immune response without, under these conditions, substantially affecting the maximal level of the humoral response.

Example 13

Titration of ppGpp for Optimal Immunological Enhancement

The relative abundance of ppGpp during the stringent response is greater than that of pppGpp. A titration was performed for different levels of ppGpp for the generation of a specific immune response. BALB/C mice were immunized by i.m. injection with 1 $\mu$g of recombinant hepatitis B surface antigen (HBsAg) alone (FIG. 3A), HBsAg plus alum (FIG. 3B), or HBsAg plus alum plus 2 $\mu$g (FIG. 3C), 10 $\mu$g (FIG. 3D), 50 $\mu$g (FIG. 3E) or 250 $\mu$g (FIG. 3F) of ppGpp. Alum was used for all injections involving ppGpp.

The optimal dosage per mouse of ppGpp under these conditions was 10 $\mu$g (FIGS. 3C–3F). Comparing the groups injected with HBsAg plus alum versus HBsAg plus alum plus 10 $\mu$g ppGpp, the ppGpp group produced significantly more anti-HBsAg antibodies than the alum group within two weeks after injection (compare FIG. 3B vs. FIG. 3D, mean ELISA titers of 83±37 ng/ml vs. 16±10 ng/ml, p=0.04). This trend was still present at 4 weeks post-immunization (FIG. 3B vs. FIG. 3D). By 6 weeks post-immunization the two groups exhibited comparable titer levels and by 10 weeks had reached similar maximal levels (2316±1764 ng/ml vs. 2328±848 ng/ml).

Figure 3:
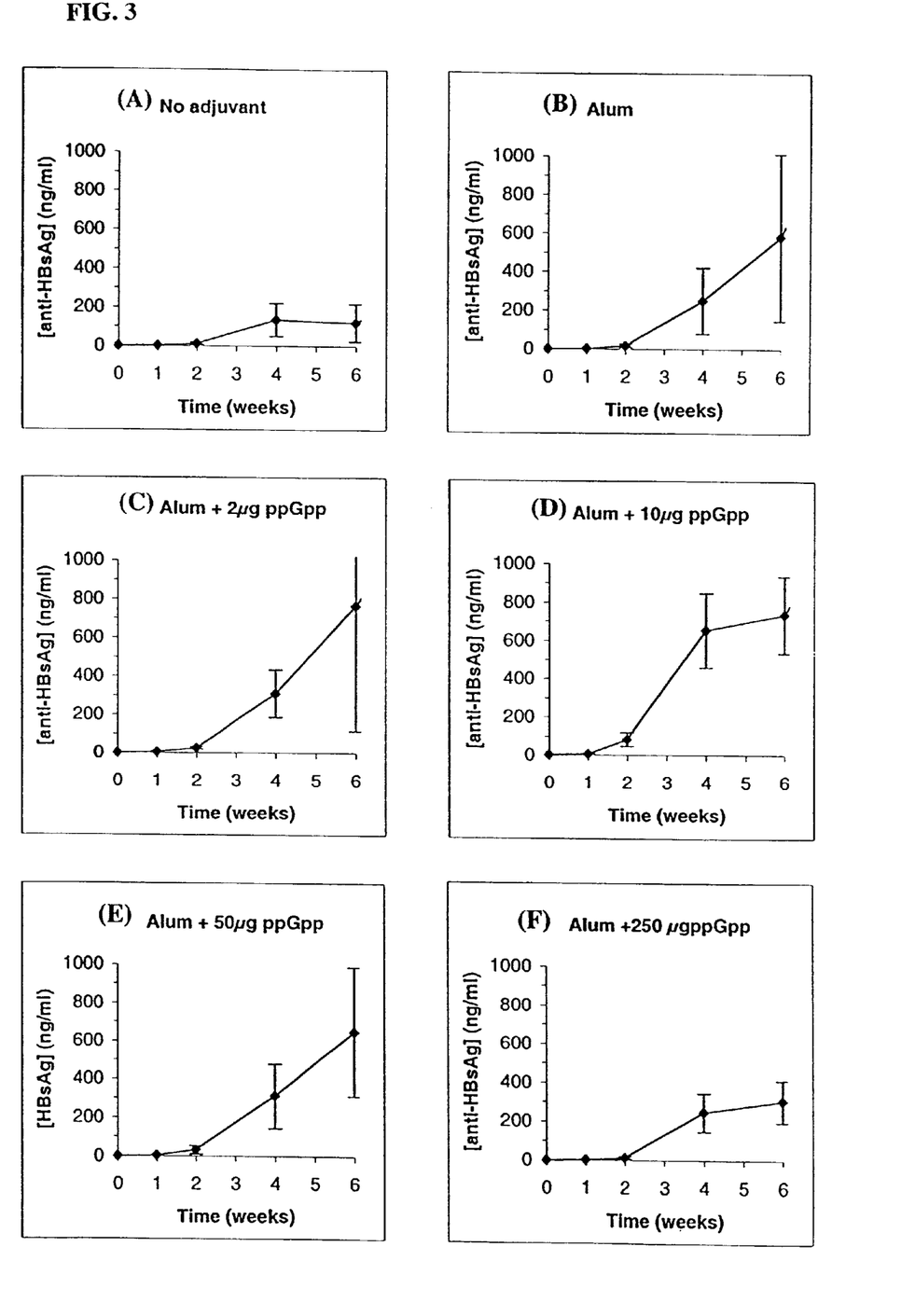

These results confirm those of the previous example—ppGpp affected the kinetics but not the magnitude of the humoral response. The effect was highly dose-dependent and was only observed at a level of 10 $\mu$g ppGpp per mouse (FIG. 3). The addition of 2 $\mu$g or 50 $\mu$g of ppGpp did not have a significant effect upon the humoral response (FIG. 3C and FIG. 3E), while 250 $\mu$g of ppGpp appeared to suppress the alum-induced adjuvant effect (FIG. 3F vs. FIG. 3B).

Treatment with ppGpp was well tolerated by all mice, as evidenced by the lack of apparent ruffling of fur, diarrhea, or other signs of toxicity, even with the 250 $\mu$g dose of ppGpp.

Example 14

Comparing the Effects of (p)ppGpp and GTP

The structures of ppGpp and pppGpp are distinguishable from those of GMP, GDP and GTP by the presence of an additional diphosphate group at the 3' position of the sugar (see FIG. 1). To determine whether the adjuvant-like effect of (p)ppGpp was due to the presence of the 3' diphosphate group, the effects of ppGpp, pppGpp, (p)ppGpp and GTP were compared. Approximately equimolar amounts of each compound (approx. 18 nmol per mouse), based on the approximate optimal dose of 10 µg ppGpp per mouse, was used (FIGS. 4A–4E). HBsAg and alum were also injected into the mice, as described above.

Mice receiving ppGpp, pppGpp or the mixture of (p)ppGpp showed a more rapid immune response than the alum control, as evidenced by significantly higher titers (p<0.05) at 2 to 3 weeks post-immunization (mean titers of 161±42, 136±33 and 171±44 ng/ml at 3 weeks versus 70±21 ng/ml). By contrast, the effects of GTP were modest at best, consistent with previous studies (Gregory and Kern, 1981). These results demonstrate that GTP, and by implication GDP, are not the active entities responsible for the adjuvant effects of ppGpp or pppGpp.

Figure 4:
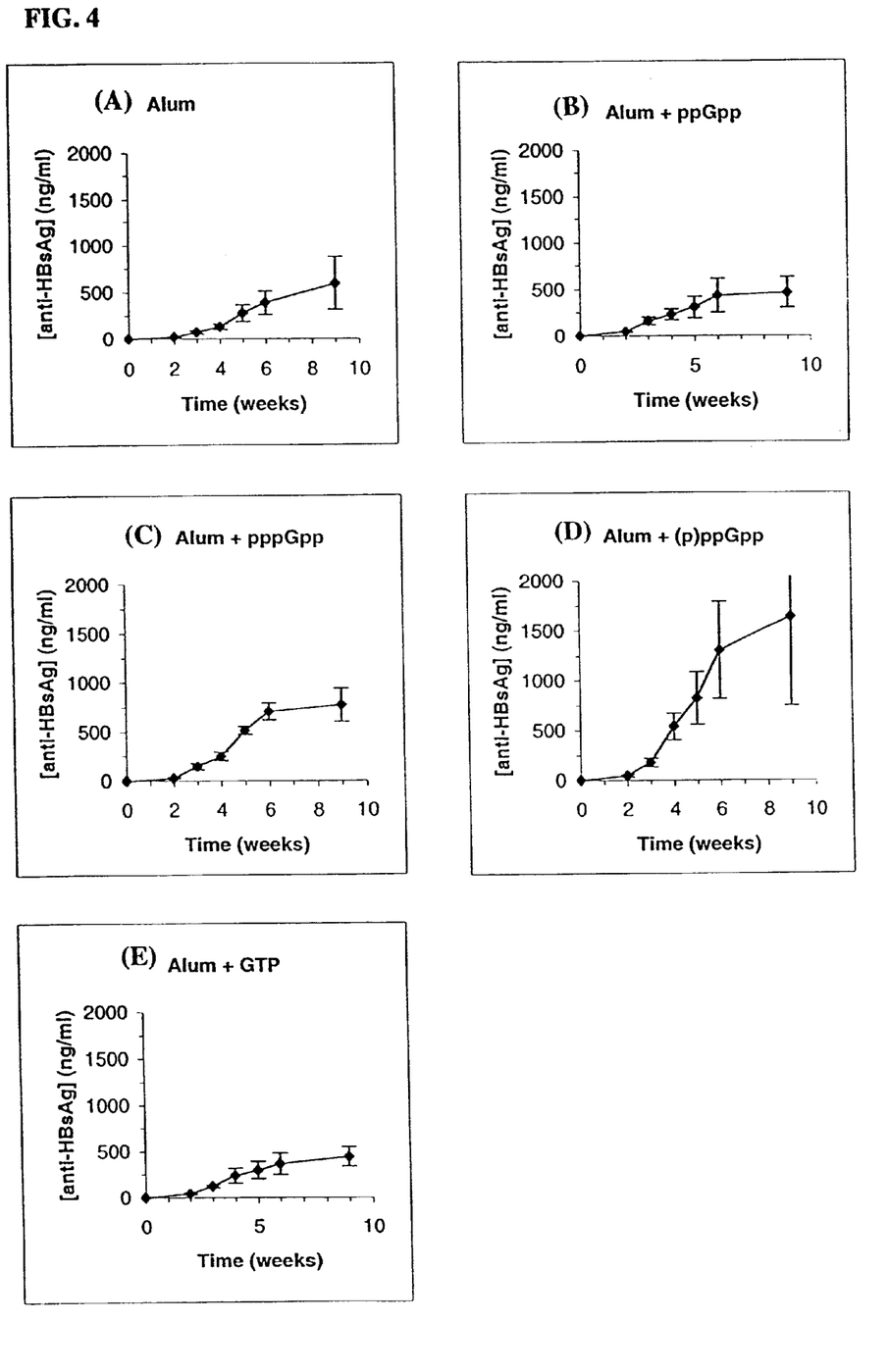

The most marked effect was observed in mice injected with combined (p)ppGpp (FIG. 4D). At 2 weeks post-immunization, the antibody titer of mice injected with (p)ppGpp and alum was significantly greater than alum alone (41±12 vs. 19±8 ng/ml, p=0.042). The heightened level of humoral response due to (p)ppGpp was maintained at least 6 weeks post-immunization (FIG. 4A vs. FIG. 4D, mean antibody titers of 1304±487 versus 382±127 ng/ml). This level was significantly higher than the titers achieved by adding either ppGpp or pppGpp separately with alum, suggesting that ppGpp and pppGpp may be stimulating the immune system through different mechanisms to give a synergistic response.

Example 15

Mechanism of Immune Response Generated

Isotype analysis (not shown) of the anti-HBsAg antibodies generated in the study described above revealed a predominance of IgG1 antibodies over IgG2a antibodies, is indicative of a Th2 (humoral) immune response rather than a Th1 (cellular) response. Alum alone induces a characteristic Th2 response (Allison and Byars, 1991). It is possible that (p)ppGpp does not affect the type of immune response per se, but influences the kinetics of the response, irrespective of its nature.

Example 16

Figure 5:
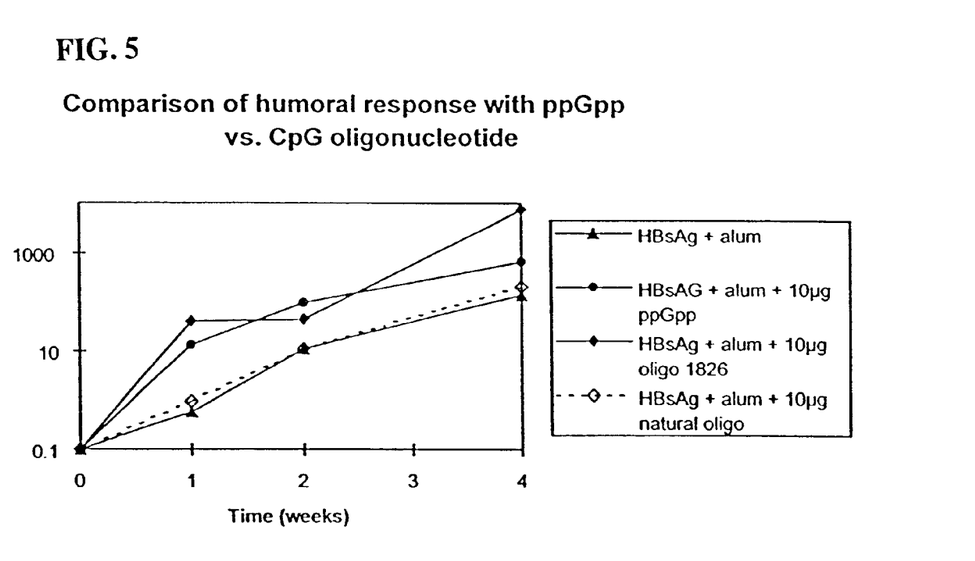

Comparison of the Kinetics and Magnitude of the Immune Response Elicited by ppGpp Versus an Oligonucleotide Containing CpG Comparison of ppGpp (10 µg) with a synthetic oligonucleotide (10 µg) containing unmethylated CpG (a very powerful adjuvant) in the presence of alum showed that the unmethylated CpG produced a greater humoral immune response in terms of magnitude (FIG. 5, note the logarithmic scale).

In this study, the time course for the humoral response did not appear to differ between ppGpp (closed circles) and the unmethylated CpG oligonucleotide (oligo 1826, closed diamonds). However, the comparison is misleading due to the order of magnitude increase in the maximal response level observed with oligo 1826. It is important to note that the CpG oligonucleotide used (oligonucleotide 1826) has been extensively optimized in terms of DNA sequence for maximum immunostimulatory effect, and contains a nuclease-resistant phosphorothioate backbone to improve cell uptake and in vivo stability (Davis et al., 1998; Krieg et al., 1995). Based on earlier reports (Krieg et al., 1995), the equivalent unmodified oligonucleotide containing a phosphodiester backbone would have to be used at concentrations more than 2 orders of magnitude greater than that of the resistant oligonucleotide to attain the same response. This predicted response is included in FIG. 5 for comparison (dotted line), and demonstrates that the natural form of ppGpp has a much greater effect than would be predicted for the natural CpG oligonucleotide.

These results are consistent with the unique effect of (p)ppGpp as an adjuvant that produces a more rapid time course for humoral response without affecting the maximal magnitude of the response.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Ada, In: Paul, E. W., ed. *Fundamental Immunology*, Third Edition, Raven Press, New York. 1309–1352, 1993.
2. Allison and Byars, *Mol. Immunol.*, 28:279–284, 1991.
3. Cashel, *Ann. Rev. Biochem.*, 57:100–107, 1974.
4. Cashel, *Ann. Rev. Microbiol.*, 29:301–318, 1975.
5. Davis, H. L., Michel, M. -L. & Whalen, R. G., *Human Molecular Genetics* 2: 1847–1851,1993.
6. Davis, Weeranta, Waldschmidt, Tygrett, Schorr Krieg, *J. Immunol.*, 160:870–876, 1998.
7. Elgert, In: *Immunology: Understanding the Immune System*, Wiley-Liss, New York, 371, 1996.
8. Gallant, *Ann. Rev. Genetics*, 13:393–415, 1979.
9. Goodman, M. G., *Biomed. Pharmacother.* 37:344–350, 1983.
10. Goodman, M. G. and Goodman, J. H., *J. Immunol.* 153:4081–4087, 1994.
11. Gregory, S. H. and Kern, M., *Immunology* 42:451–457, 1981.
12. Heeg, Sparwasser, Lipford, Hacker, Zimmermann, Wagner, *Eur. J. Clin. Microbiol. Infec. Dis.*, 17:464–469, 1998.
13. Krieg A., Yi, Matson, Waldschmidt, Bishop, Teasdale, Koretzky, Klinman, *Nature* 374:546–549, 1995.
14. Lipford G B, Heeg K, Wagner, *Trends Microbiol.*, 6(12):496–500, 1998.
15. Livingston, P. O., *Immunol. Rev.* 145: 147–166, 1995.
16. Marrack and Kappler, *Cell,* 76:323–332, 1994.
17. Murphy, Infect. Dis. Clin. Pract. 2:174–181, 1993.
18. Reitz et al., *J. Med. Chem.* 37:3561–3578.
19. Robinson, A., Farrar, G. H. & Wiblin, C. N., *Vaccine Protocols,* Humana Press, Totowa, N.J., 1996.
20. Roitt, Brostoff, Male, In: *Immunology,* Mosby, London, 19.8–19.9, 1996.
21. Roitt, In: *Essential Immunlogy,* Blackwell Scientific Publications, London. 288–292, 1994.
22. Scheuer et al., *Cell. Immunol.* 91:294–300, 1985.

23. Sjolander, Cox, Barr, *J. Leuco. Biol.*, 64:713–723, 1998.
24. Subbarao et al., *J. Virol.* 67:7223–7228, 1993.
25. Stewart-Tull, D. E. S., ed., *The Theory and Practical Application of Adjuvants*, Wiley, Chichester and New York.
26. U.S. Pat. No. 5,470,967
27. U.S. Pat. No. 5,672,697
28. U.S. Pat. No. 5,714,606

What is claimed is:

1. A pharmaceutical composition comprising an antigen and a nucleotide in a pharmaceutically acceptable carrier, wherein the nucleotide is selected from the group consisting of guanosine tetraphosphate (ppGpp) and guanosine pentaphosphate (pppGpp), and wherein the administration of the composition to the host results in a more rapid response of the host immune system against the antigen.

2. The pharmaceutical composition of claim 1, further comprising alum.

3. The pharmaceutical composition of claim 1, further defined as comprising a mixture ((p)ppGpp) of guanosine tetraphosphate and guanosine pentaphosphate.

4. A pharmaceutical composition comprising alum and a nucleotide in a pharmaceutically acceptable carrier, wherein the nucleotide is selected from the group consisting of guanosine tetraphosphate (ppGpp) and guanosine pentaphosphate (pppGpp), and wherein the administration of the composition to the host results in a more rapid response of the host immune system.

5. The composition of claim 4, further comprising an antigen.

6. The pharmaceutical composition of claim 4, further defined as comprising a mixture ((p)ppGpp) of guanosine tetraphosphate and guanosine pentaphosphate.

7. A pharmaceutical composition comprising alum, an antigen and a nucleotide in a pharmaceutically acceptable carrier, wherein the nucleotide is selected from the group consisting of guanosine tetraphosphate (ppGpp) and guanosine pentaphosphate (pppGpp), and wherein the administration of the composition to the host results in a more rapid response of the host immune system against the antigen.

8. The pharmaceutical composition of claim 7, further defined as comprising a mixture ((p)ppGpp) of guanosine tetraphosphate and guanosine pentaphosphate (pppGpp).

9. The pharmaceutical composition of claim 1, wherein the nucleotide is guanosine tetraphosphate (ppGpp).

10. The pharmaceutical composition of claim 1, wherein the nucleotide is guanosine pentaphosphate (pppGpp).

11. The pharmaceutical composition of claim 4, wherein the nucleotide is guanosine tetraphosphate (ppGpp).

12. The pharmaceutical composition of claim 4, wherein the nucleotide is guanosine pentaphosphate (pppGpp).

13. The pharmaceutical composition of claim 7, wherein the nucleotide is guanosine tetraphosphate (ppGpp).

14. The pharmaceutical composition of claim 7, wherein the nucleotide is guanosine pentaphosphate (pppGpp).

* * * * *

UNITED STATES PATENT AND TRADEMARK OFFICE
CERTIFICATE OF CORRECTION

PATENT NO. : 6,562,801 B1
DATED : May 13, 2003
INVENTOR(S) : Rombel

It is certified that error appears in the above-identified patent and that said Letters Patent is hereby corrected as shown below:

<u>Title page,</u>
Item [57], ABSTRACT,
Line 7, delete "was" and insert therefor -- as --.

Signed and Sealed this

Second Day of December, 2003

JAMES E. ROGAN
*Director of the United States Patent and Trademark Office*